United States Patent
Beroza et al.

(10) Patent No.: US 8,410,163 B2
(45) Date of Patent: Apr. 2, 2013

(54) SUBSTITUTED 4-AMINO-5-BENZOYL- 2-(PHENYLAMINO)THIOPHENE-3-CARBONITRILES AND SUBSTITUTED 4-AMINO- 5-BENZOYL-2-(PHENYLAMINO)THIOPHENE-3-CARBOXAMIDES AS TUBULIN POLYMERIZATION INHIBITORS

(75) Inventors: Paul P. Beroza, Belmont, CA (US); Komath V. Damodaran, Cupertino, CA (US); Stella Lui, Daly City, CA (US); Wenli Ma, Union City, CA (US); Zhuo Wang, Fremont, CA (US); Hua Xu, Sunnyvale, CA (US)

(73) Assignee: Telik, Inc., Palo Alto, CA (US)

( * ) Notice: Subject to any disclaimer, the term of this patent is extended or adjusted under 35 U.S.C. 154(b) by 0 days.

(21) Appl. No.: 13/263,489

(22) PCT Filed: Feb. 9, 2010

(86) PCT No.: PCT/US2010/023561
§ 371 (c)(1),
(2), (4) Date: Dec. 19, 2011

(87) PCT Pub. No.: WO2010/120400
PCT Pub. Date: Oct. 21, 2010

(65) Prior Publication Data
US 2012/0101286 A1    Apr. 26, 2012

Related U.S. Application Data

(60) Provisional application No. 61/169,785, filed on Apr. 16, 2009.

(51) Int. Cl.
*A61K 31/381* (2006.01)
*C07D 409/10* (2006.01)
*C07D 333/38* (2006.01)

(52) U.S. Cl. ............ 514/444; 514/447; 549/60; 549/61; 549/68

(58) Field of Classification Search .................... 549/60, 549/68, 61
See application file for complete search history.

(56) References Cited

U.S. PATENT DOCUMENTS
2006/0041006 A1    2/2006 Ibrahim et al.

FOREIGN PATENT DOCUMENTS
WO    WO-2005/033102 A2    4/2005

OTHER PUBLICATIONS

International Preliminary Report on Patentability for PCT/US2010/023561, dated Oct. 27, 2011.
International Search Report for PCT/US2010/023561, dated Oct. 22, 2010.
Sauter et al., "Syntheses neuer derivate des 2-amino-4,5,6,7-tetrahydrobenzo[b]thiophen-3-carbonitrils: basische substitutionsprodukte and anellierte thieno-[1,2,4]-triazolo-pyrimidine", Monatshefte fur Chemie, 106, 1111-1116 (1975).
Toche et al., "Synthesis of novel pyrano fused quinolones, coumarins, and pyridones", J. Heterocyclic Chem., 36, 467-471 (1999).

*Primary Examiner* — Kristin Bianchi
(74) *Attorney, Agent, or Firm* — Foley & Lardner LLP

(57) ABSTRACT

Substituted 4-amino-5-benzoyl-2-(phenylamino)thiophene-3-carbonitriles and substituted 4-amino-5-benzoyl-2-(phenylamino)thiophene-3-carboxamides and their salts are tubulin polymerization inhibitors, useful in the treatment of cancer.

13 Claims, No Drawings

SUBSTITUTED 4-AMINO-5-BENZOYL-2-(PHENYLAMINO)THIOPHENE-3-CARBONITRILES AND SUBSTITUTED 4-AMINO-5-BENZOYL-2-(PHENYLAMINO)THIOPHENE-3-CARBOXAMIDES AS TUBULIN POLYMERIZATION INHIBITORS

CROSS-REFERENCE TO RELATED APPLICATION

This application claims the benefit under 35 USC 119(e) of U.S. Provisional Patent Application No. 61/169,785, filed 16 Apr. 2009, entitled "Substituted 4-amino-5-benzoyl-2-(phenylamino)thiophene-3-carbonitriles and -3-carboxamides as tubulin polymerization inhibitors", the entire disclosure of which is incorporated into this application by reference.

TECHNICAL FIELD

This invention relates to substituted 4-amino-5-benzoyl-2-(phenylamino)thiophene-3-carbonitriles and 4-amino-5-benzoyl-2-(phenylamino)thiophene-3-carboxamides, their salts, pharmaceutical compositions containing them, and their use as tubulin polymerization inhibitors and in the treatment of cancer.

BACKGROUND ART

Microtubules are cytoskeleton protein polymers comprised of α-tubulin and β-tubulin polymers. They are vital components of all cells and are critical for the maintenance of cell morphology. Microtubules form the basis of the mitotic apparatus in cells, and dynamically functioning microtubules are critical for normal cell division, as well as cell movement and attachment. Interference with microtubule dynamics prevents dividing cells from proceeding normally through the cell cycle and leads to G2/M cell cycle arrest and apoptosis. Cancer cells acquire unlimited replicative potential and continually divide without going into quiescence or senescence. As a result, cancer cells are extremely dependent upon microtubule dynamics and thus are susceptible to agents that interfere with microtubule dynamics either through inhibiting tubulin polymerization or stabilizing microtubule polymers.

During the M-phase of the cell cycle, the dynamic microtubules that comprise the cell mitotic spindle are the target of most of the known tubulin-directed agents. Although the ultimate mechanism of action of the various anti-mitotic agents is essentially the same (i.e. disruption of normal microtubule formation and dynamics), there are differences in the activity of the various agents against different cancer types. For example, the vinca alkaloids (such as vincristine, vinblastine, and vinorelbine) are generally more efficacious against hematological cancers and less effective against solid tumors, though vinorelbine has activity in non-small cell lung cancer and breast cancer; while the taxanes (such as paclitaxel and docetaxel) are effective against ovarian, breast and lung solid tumors, but are relatively ineffective against solid tumors of the colon and kidney and against hematological cancers.

It would be desirable to develop compounds that are potent inhibitors of tubulin polymerization as anticancer agents.

US Patent Application Publication No. US 2005/0085531 (Amphora) discloses 544 thiophene-based compounds said to exhibit ATP-utilizing enzyme inhibitory activity. These compounds include 4-amino-5-benzoyl-2-[(2-methoxyphenyl)amino]thiophene-3-carbonitrile, said to be an inhibitor of GSK-3α, GSK-3β, KIT, and MAPKAPK; 4-amino-5-benzoyl-2-(phenylamino)thiophene-3-carboxamide, said to be an inhibitor of Aurora-A, GSK-3α, GSK-3β, and KIT; and 4-amino-2-(1,3-benzodioxol-5-ylamino)-5-(4-chlorobenzoyl)thiophene-3-carboxamide (compound 27A below), said to be an inhibitor of Aurora-A, GSK-3α, and GSK-3β. No specific activities are given, though the compounds are said to have an activity for each of the listed target enzymes greater than 3σ from the mean activity for the population of predominately inactive compounds for the same target enzyme.

US Patent Application Publication No. US 2006/0041006 (Plexxikon) discloses 281 thiophene-based compounds said to be ligands for phosphodiesterase (PDE) 4B, and their use in treating PDE4B-mediated conditions. These compounds include 43 4-amino-5-benzoyl-2-(phenylamino)thiophene-3-carbonitriles, including 4-amino-5-(2,4-dimethoxybenzoyl)-2-[(4-methoxyphenyl)amino]thiophene-3-carbonitrile (compound 7A below), and one 4-amino-5-benzoyl-2-(phenylamino)thiophene-3-carboxamide.

Graschenkova et al., *Farmatsevtichnii Zhurnal*, 4, 69-73 (2007), is said to disclose the synthesis and hypolipidemic activity of various 2-aroyl-3-amino-4-nitryl-5-arylaminothiophenes. According to the abstract and indexing from Chemical Abstracts, the compound 4-amino-5-(4-chlorobenzoyl)-2-[(4-ethylphenyl)amino]thiophene-3-carbonitrile (compound 15A below) was said to be disclosed.

A number of substituted 4-amino-5-benzoyl-2-(phenylamino)thiophene-3-carbonitriles and 4-amino-5-benzoyl-2-(phenylamino)thiophene-3-carboxamides, including compounds 1A, 4A, 12A, 17A, and 38A below, are available from scientific catalogs.

The entire disclosures of all of the documents referred to in this application are incorporated into this application by reference.

DISCLOSURE OF THE INVENTION

In a first aspect, this invention is the use of substituted 4-amino-5-benzoyl-2-(phenylamino)thiophene-3-carbonitriles and substituted 4-amino-5-benzoyl-2-(phenylamino)thiophene-3-carboxamides of formula A:

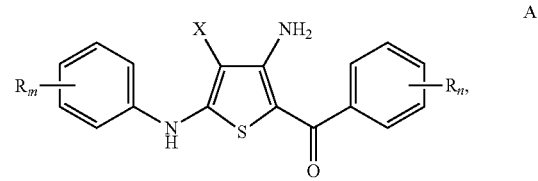

and their salts,
where:
X is CN or $CONH_2$;
m and n independently are 0, 1, 2, or 3, provided that at least one of m and n is not 0; and
each R independently is halo, cyano, nitro, or optionally substituted alkyl, or is —OR', —SR', —C(O)OR', or —NR'R", where R' is optionally substituted alkyl, and R" is hydrogen or alkyl, or two adjacent R groups on the same phenyl group together are methylenedioxy, as tubulin polymerization inhibitors and for use in the treatment of diseases capable of treatment by a tubulin polymerization inhibitor, particularly cancer; pharmaceutical compositions comprising the compounds for use as tubulin polymerization inhibitors and for use in the treatment of diseases capable of treatment by a tubulin polymerization inhibitor, particularly cancer; the use of the compounds in the manufacture of medicaments for use as a tubulin polymerization inhibitor and for use in the treatment of diseases capable of treatment by a tubulin polymerization inhibitor, particularly cancer; and methods of treatment of diseases capable of treatment by a tubulin polymerization inhibitor, particularly cancer, by administration of the compounds.

In a second aspect, this invention is the compounds 1A, 4A, 12A, 17A, and 38A as pharmaceutical agents, pharmaceutical compositions comprising the compounds, the use of the compounds in the manufacture of medicaments and for use in the treatment of diseases by administration of the compounds.

This invention also includes novel compounds within those compounds described in the first aspect of this invention, such as the compounds 2A, 3A, 5A, 6A, 8A to 11A, 13A, 14A, 16A, 18A to 26A, 28A to 37A, and 39A to 41A below, and their salts, and pharmaceutical compositions containing them; their use as medicaments and in the manufacture of medicaments; and methods of treatment by their administration, as described in the first and second aspects of this invention. Each of these compounds is disclosed individually, and in all combinations.

Preferred embodiments of this invention are characterized by the specification and by the features of the claims of this application as filed.

MODES FOR CARRYING OUT THE INVENTION

Definitions

"Alkyl" means a monovalent group derived from a saturated $C_{1-3}$ hydrocarbon that may be linear, branched, or cyclic, by removal of one hydrogen atom from a carbon atom, i.e. methyl, ethyl, propyl, isopropyl, and cyclopropyl. Note that the definition of "alkyl" in this application is broader than the conventional definition and includes a group more commonly referred to as "cycloalkyl".

A "substituted alkyl" is an alkyl, as defined above, substituted with up to three halogen atoms and/or a substituent selected from —CN, —OR, —SR, and —NR$_2$, where each R independently is hydrogen or alkyl. Thus, for example, substituted alkyl groups include such groups as trifluoromethyl, 2-(dimethylamino)ethyl, and 3-chloropropyl.

"Halogen" or "halo" means F, Cl, or Br.

"Salts" are described in the section entitled "Compounds of this invention".

A "therapeutically effective amount" means that amount which, when administered to a human for treating a cancer, is sufficient to effect treatment for the cancer. "Treating" or "treatment" of a cancer in a human includes one or more of:
(1) limiting/inhibiting growth of the cancer, i.e., limiting/arresting its development,
(2) reducing/preventing spread of the cancer, i.e. reducing/preventing metastases,
(3) relieving the cancer, i.e., causing regression of the cancer,
(4) reducing/preventing recurrence of the cancer, and
(5) palliating symptoms of the cancer.

"Combination therapy" means the administration of a compound of this invention and another therapy for the disease being treated, especially another anticancer therapy during the course of cancer chemotherapy. Such combination therapy may involve the administration of the compound of the first aspect of this invention before, during, and/or after the administration of the another therapy. The administration of the compound of the first aspect of this invention may be separated in time from the administration of the another therapy by up to several weeks, and may precede it or follow it, but more commonly the administration of the compound of the first aspect of this invention will accompany at least one aspect of the another therapy (in the case of anticancer therapy, such as the administration of one dose of a chemotherapeutic agent, molecular targeted therapy agent, biologic therapy agent, or radiation therapy) within up to 48 hours, and most commonly within less than 24 hours.

"Another therapy" is a therapy for the disease that is not a treatment with a compound of this invention. Such "another therapies" for cancers include chemotherapy; molecular targeted therapy; biologic therapy; and radiotherapy. These therapies are those used as monotherapy or in combination therapy.

Chemotherapeutic agents for cancer include alkylating agents, antimetabolites, natural products including antitumor antibiotics, anthracyclines, enzymes, taxanes, vinca alkaloids, camptothecins, and etoposide, hormones and hormone antagonists, and miscellaneous agents, including altretamine, arsenic trioxide, gallium nitrate, hydroxyurea, levamisole, mitotane, octreotide, procarbazine, suramin, thalidomide, lenalidomide, photodynamic compounds such as methoxsalen and sodium porfimer, and proteasome inhibitors such as bortezomib.

Molecular targeted therapy agents for cancer include functional therapeutic agents, phenotype-directed therapy agents including monoclonal antibodies, and cancer vaccines.

Biologic therapy agents for cancer include interferons and interleukins.

In addition to these agents intended to act against cancer cells, anticancer therapies include the use of protective or adjunctive agents, including cytoprotective agents such as amifostine, dexrazoxane, and mesna; phosphonates such as pamidronate and zoledronic acid; and stimulating factors such as epoetin, darbeopetin, filgrastim, PEG-filgrastim, and sargramostim.

Combination cancer therapy regimens with which the compounds of this invention may be combined include all regimens involving the use of two or more of the anticancer therapies (anticancer agents) such as those mentioned herein and/or radiotherapy, optionally including protective and adjunctive agents such as those mentioned herein; and the compound of this invention can be added to existing anticancer regimens known for the treatment of various cancers, such as the regimens mentioned in such books as Chabner and Longo, eds., "Cancer Chemotherapy and Biotherapy: Principles and Practice", 3rd ed. (2001), and Skeel, ed., "Handbook of Cancer Chemotherapy", 6th ed. (2003), both from Lippincott Williams & Wilkins, Philadelphia, Pa., U.S.A.; and regimens for anticancer therapies, especially chemotherapies, may be found on Web sites such as those maintained by the National Cancer Institute (www.cancer.gov), the American Society for Clinical Oncology (www.asco.org), and the National Comprehensive Cancer Network (www.nccn.org).

"Comprising" or "containing" and their grammatical variants are words of inclusion and not of limitation and mean to specify the presence of stated components, groups, steps, and the like but not to exclude the presence or addition of other components, groups, steps, and the like. Thus "comprising" does not mean "consisting of", "consisting substantially of", or "consisting only of"; and, for example, a formulation "comprising" a compound must contain that compound but also may contain other active ingredients and/or excipients.

Compounds of this Invention

Salts (for example, pharmaceutically acceptable salts) of the compounds of formula A are included in the present invention and are useful in the compositions, methods, and uses described in this application. Such salts are preferably formed with pharmaceutically acceptable acids. See, for example, Stahl and Wermuth, eds., "Handbook of Pharmaceutically Acceptable Salts", (2002), Verlag Helvetica Chimica Acta, Zürich, Switzerland, for an extensive discussion of pharmaceutical salts, their selection, preparation, and use. Unless the context requires otherwise, reference to any compound of this invention is a reference both to the compound and to its salts.

These salts include salts that may be formed when acidic protons present are capable of reacting with inorganic or organic bases. Typically the parent compound is treated with an excess of an alkaline reagent, such as hydroxide, carbonate or alkoxide, containing an appropriate cation. Cations such as $Na^+$, $K^+$, $Ca^{2+}$, $Mg^{2+}$ and $NH_4^+$ are examples of cations present in pharmaceutically acceptable salts. Suitable inorganic bases, therefore, include calcium hydroxide, potassium hydroxide, sodium carbonate and sodium hydroxide. Salts may also be prepared using organic bases, such as salts of primary, secondary and tertiary amines, substituted amines including naturally-occurring substituted amines, and cyclic amines including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like.

If a compound of the first aspect of this invention contains a basic group, such as an $-NR_2$ group, it may be prepared as an acid addition salt. Acid addition salts of the compounds are prepared in a standard manner in a suitable solvent from the parent compound and an excess of an acid, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, 4-toluenesulfonic acid, hexanoic acid, heptanoic acid, cyclopentanepropionic acid, lactic acid, 2-(4-hydroxybenzoyl)benzoic acid, 1,2-ethanedisulfonic acid, 2-hydroxyethanesulfonic acid, benzenesulfonic acid, 4-chlorobenzenesulfonic acid, 2-naphthalenesulfonic acid, camphorsulfonic acid, 4-methylbicyclo[2.2.2.]oct-2-ene-1-carboxylic acid, glucoheptonic acid, gluconic acid, 4,4'-methylenebis(3-hydroxy-2-naphthoic)acid, 3-phenylpropionic acid, trimethylacetic acid, tert-butylacetic acid, laurylsulfuric acid, glucuronic acid, glutamic acid, 3-hydroxy-2-naphthoic acid, stearic acid, muconic acid and the like.

Representative compounds of this invention include those compounds of formula A where one or more of the following is true:
(1a) X is CN; or
(1b) X is $CONH_2$;
(2) m is at least 1, preferably 1 or 2;
(3) n is at least 1, preferably 1 or 2; and
(4) at least one R is on the 4-position of the phenyl to which it is attached (taking the 1-position as being the point of attachment to the carbonyl or amino group linking the phenyl to the thiophene), or if two Rs together are methylenedioxy, then the methylenedioxy is attached at the 3- and 4-positions of the phenyl; preferably both phenyls are substituted on the 4-position by an R or one phenyl is substituted on the 4-position by an R and the other phenyl is substituted with a 3,4-methylenedioxy.

Generally, a compound having a greater number of these features is preferred over a compound having a lesser number of these features; in particular, addition of one of these features to a compound having less than all the features will generally result in a compound that is preferred over the compound without that feature.

Compounds of this invention include each of the compounds described in the specification and claims of this application as filed, including in the Examples and the compound table below, such as compounds 2A, 3A, 5A, 6A, 8A to 11A, 13A, 14A, 16A, 18A to 26A, 28A to 37A, and 39A to 41A; especially compounds 2A, 3A, 5A, 6A, 8A to 11A, 13A, 14A, and 16A; particularly compounds 6A and 10A; and their salts. Compositions and methods, etc., of this invention include compositions and methods, etc., where the compound is one of those compounds enumerated in the preceding sentence, together with compounds 1A, 4A, 7A, 12A, 15A, 17A, 27A, and 38A.

For simplicity and consistency, each of the compounds of formula A are named in this specification and claims as a derivative of 4-amino-5-benzoyl-2-(phenylamino)thiophene-3-carbonitrile or 4-amino-5-benzoyl-2-(phenylamino)thiophene-3-carboxamide rather than by following the following the priority rules of IUPAC naming conventions. Thus, for example, compound 6A, the compound of the formula

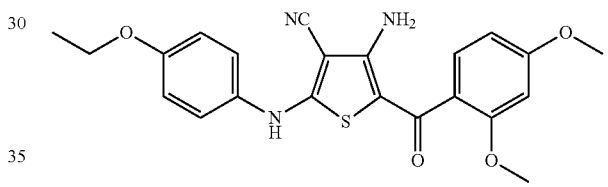

is named 4-amino-5-(2,4-dimethoxybenzoyl)-2-[(4-ethoxyphenyl)amino]thiophene-3-carbonitrile; and compound 1A, the compound of the formula

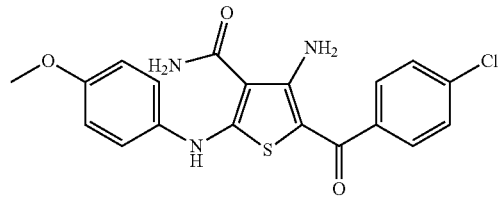 [SMILES: COc1ccc(Nc2sc(C(=O)c3ccc(Cl)cc3)c(N)c2C(N)=O)cc1]

is named 4-amino-5-(4-chlorobenzoyl)-2-[(4-methoxyphenyl)amino]thiophene-3-carboxamide.

Preparation of the Compounds

In the reaction scheme shown below in the discussion of the general synthetic methods, no substituents are shown on either benzene ring, but it will be apparent that substituents (either the final substituents on the desired compound, or precursors to those final substituents to be modified after formation of the compound core) may be present, as discussed later in the specification and as illustrated by the Examples.

A convenient general synthetic method, applicable to both the carbonitriles and carboxamides, involves the reaction of the anion of malononitrile or 2-cyanoacetamide with a phenyl isothiocyanate and a 2-L-acetophenone, and is illustrated below.

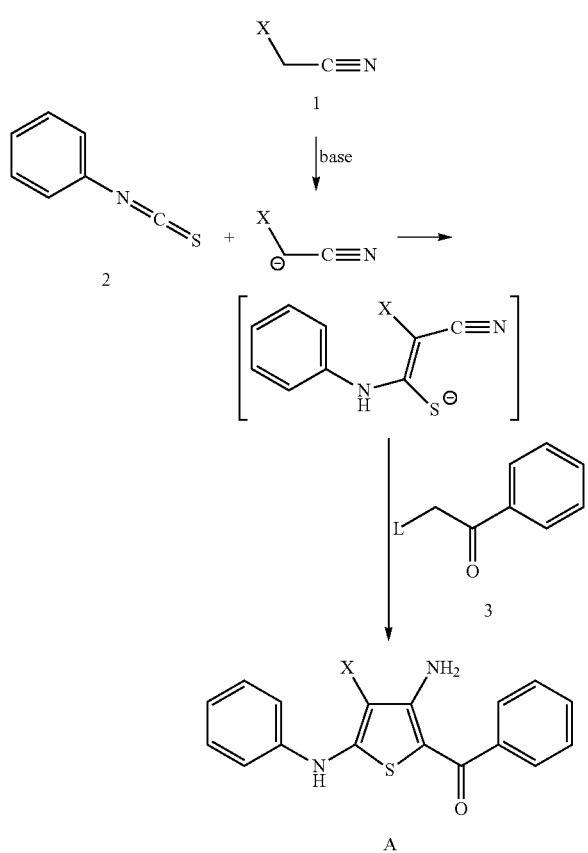

Malononitrile (1, X=CN) or 2-cyanoacetamide (1, X=CONH$_2$), dissolved in a polar solvent such as dimethylformamide, is treated with a base to form the corresponding anion. When malononitrile is used, the base may be a weak base, such as potassium carbonate; but when 2-cyanoacetamide is used, the base is generally a stronger base such as a metal hydride or ethoxide. The phenyl isothiocyanate (2) is then added, followed by the 2-L-acetophenone (3, L is a leaving group such as bromine, chlorine, alkylsulfonyloxy, or arylsulfonyloxy, especially bromine). The resulting carbonitrile/carboxamide product of formula A may conveniently isolated by addition of water, optionally preceded by removal of the solvent, to precipitate the crude product; and may be purified by conventional means, for example chromatography on silica gel.

Malononitrile and 2-cyanoacetamide are commercially available, as are many phenyl isothiocyanates and 2-L-acetophenones such as 2-bromoacetophenones. Phenyl isothiocyanates also may be prepared from their corresponding anilines by reaction with thiophosgene (and the anilines also prepared from the corresponding nitrobenzenes by reduction); and 2-bromoacetophenones also may be prepared from their corresponding acetophenones by reaction with bromine in acetic acid, allowing the convenient preparation of a large number of starting materials and hence compounds of formula A.

Compounds of formula A may be converted to salts by reaction with the appropriate acids, using techniques well known to a person of ordinary skill in the art for the formation of acid addition salts. The acid used, and the reaction conditions, may be chosen to give salts that are pharmaceutically acceptable and that have a form convenient for isolation and formulation, such as a solid form (for example, amorphous or crystalline).

Compounds for a Use, Compositions, and Uses

The compounds of this invention may be administered by any route suitable to the subject being treated and the nature of the subject's condition. Routes of administration include administration by injection, including intravenous, intraperitoneal, intramuscular, and subcutaneous injection, by transmucosal or transdermal delivery, through topical applications, nasal spray, suppository and the like or may be administered orally. Formulations may optionally be liposomal formulations, emulsions, formulations designed to administer the drug across mucosal membranes or transdermal formulations. Suitable formulations for each of these methods of administration may be found, for example, in *Remington: The Science and Practice of Pharmacy,* 20th ed., A. Gennaro, ed., Lippincott Williams & Wilkins, Philadelphia, Pa., U.S.A. Typical formulations will be either oral or solutions for intravenous infusion. Typical dosage forms will be tablets or capsules for oral administration, solutions for intravenous infusion, and lyophilized powders for reconstitution as solutions for intravenous infusion.

Depending on the intended mode of administration, the pharmaceutical compositions may be in the form of solid, semi-solid or liquid dosage forms, preferably in unit dosage form suitable for single administration of a precise dosage. In addition to an effective amount of the active compound(s), the compositions may contain suitable pharmaceutically-acceptable excipients, including adjuvants which facilitate processing of the active compounds into preparations which can be used pharmaceutically. "Pharmaceutically acceptable excipient" refers to an excipient or mixture of excipients which does not interfere with the effectiveness of the biological activity of the active compound(s) and which is not toxic or otherwise undesirable to the subject to which it is administered.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in water or an aqueous excipient, such as, for example, water, saline, aqueous dextrose, and the like, to form a solution or suspension. If desired, the pharmaceutical composition to be administered may also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

For oral administration, the composition will generally take the form of a tablet or capsule, or it may be an aqueous or nonaqueous solution, suspension or syrup. Tablets and capsules are preferred oral administration forms. Tablets and capsules for oral use will generally include one or more commonly used excipients such as lactose and corn starch. Lubricating agents, such as magnesium stearate, are also typically added. When liquid suspensions are used, the active agent may be combined with emulsifying and suspending excipients. If desired, flavoring, coloring and/or sweetening agents may be added as well. Other optional excipients for incorporation into an oral formulation include preservatives, suspending agents, thickening agents, and the like.

Injectable formulations can be prepared in conventional forms, either as liquid solutions or suspensions, solid forms suitable for solubilization or suspension in liquid prior to injection, or as emulsions or liposomal formulations. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media.

The pharmaceutical compositions of this invention may also be formulated in lyophilized form for parenteral administration. Lyophilized formulations may be reconstituted by addition of water or other aqueous medium and then further diluted with a suitable diluent prior to use. The liquid formulation is generally a buffered, isotonic, aqueous solution. Examples of suitable diluents are isotonic saline solution, 5% dextrose in water, and buffered sodium or ammonium acetate solution. Pharmaceutically acceptable solid or liquid excipients may be added to enhance or stabilize the composition, or to facilitate preparation of the composition.

Typically, a pharmaceutical composition of the present invention is packaged in a container with a label, or instructions, or both, indicating use of the pharmaceutical composition in the treatment of a disease treatable by administration of a tubulin polymerization inhibitor, particularly cancer.

The pharmaceutical composition may additionally contain one or more other pharmacologically active agents in addition to a compound of this invention. These additional active agents will typically be useful in treating cancer, or for enhancing the treatment of cancer by compounds of this invention.

Methods of Using the Compounds

The compounds of the first aspect of this invention have activity against human cancer cell lines, as demonstrated in the in vitro and in vivo Examples below, and are therefore considered to be useful as human cancer chemotherapeutic agents, for the treatment of human cancers.

Thus, this invention includes methods of treating cancer in humans by administering a therapeutically effective amount of a compound of this invention, or a pharmaceutical composition containing it, to the human; and to the use of the compounds of this invention in the manufacture of medicaments for the treatment of cancer in humans. Optionally, the methods further comprise treating the human with another anticancer therapy, such as a therapy already conventional for the cancer being treated.

Cancers that are particularly treatable by the method of this invention are cancers with sensitivity to tubulin polymerization inhibitors. Such cancers include those mentioned herein, such as hematological malignancies, such as leukemias, lymphomas, and myelodysplastic syndrome. Other cancers particularly treatable by the method of this invention include solid malignancies such as colorectal, lung, breast, ovarian, pancreatic, bladder, brain, gastrointestinal, and kidney cancers, and hematological malignancies, such as leukemias, especially ALL and CML, lymphomas, and myelodysplastic syndrome.

The amount of the compound of this invention that is administered to the human (either alone or, more usually, in a composition of this invention) should be a therapeutically effective amount when used alone or when used in conjunction with the another anticancer therapy (if the compound of this invention is administered in conjunction with another anticancer therapy); and similarly the amount of the another anticancer therapy that is administered to the human (if the compound of this invention is administered in conjunction with another anticancer therapy) should be a therapeutically effective amount when used in conjunction with the compound of this invention. However, the therapeutically effective amount of either the compound of this invention and the amount of the another anticancer therapy when administered in combination cancer chemotherapy may each be less than the amount which would be therapeutically effective if delivered to the human alone. It is common in cancer therapy, though, to use the maximum tolerated dose of the or each therapy, with a reduction only because of common toxicity of the therapies used or potentiation of the toxicity of one therapy by another.

The compounds of this invention, or pharmaceutical compositions containing them, are thus used to treat cancer in humans requiring such treatment, by administering a therapeutically effective amount of the chosen compound or composition. Therapeutically effective amounts of compounds of the invention are in the range of 10-10,000 mg/m$^2$, for example, 30-3000 mg/m$^2$ or 100-1000 mg/m$^2$. Dosing may be at 1-35 day intervals; for example, about 500-1000 mg/m$^2$ at 1-5 week intervals, especially at 1, 2, 3, or 4 week intervals, or at higher frequencies including as frequently as once/day for several (e.g. 5 or 7) days, with the dosing repeated every 2, 3, or 4 weeks, or constant infusion for a period of 6-72 hours, also with the dosing repeated every 2, 3, or 4 weeks. Suitable dosages and dose frequencies will be readily determinable by a person of ordinary skill in the art having regard to that skill and this disclosure. No unacceptable toxicological effects are expected when compounds of the invention are administered in accordance with the present invention.

A person of ordinary skill in the art of cancer therapy will be able to ascertain a therapeutically effective amount of the compound of this invention and a therapeutically effective amount of another anticancer therapy (if the compound of this invention is administered as a part of a chemotherapeutic combination) for a given cancer and stage of disease without undue experimentation and in reliance upon personal knowledge and the disclosure of this application.

EXAMPLES

The following examples illustrate the preparation of compounds of this invention, and their activity in predictive in vitro and in vivo anticancer assays. These results are considered predictive of efficacy in human anticancer chemotherapy, as other anticancer agents tested in these assays have shown anticancer activity in humans. They are given to enable a person of ordinary skill in the art to more clearly understand and practice this invention, and should not be considered as limiting the scope of this invention but merely as illustrating and representing the invention.

Preparative and Synthetic Examples

The compounds of this invention are prepared by conventional methods of organic chemistry. See, for example, Larock, "Comprehensive Organic Transformations", Wiley-VCH, New York, N.Y., U.S.A. In some cases, protective groups may be introduced and later removed. Suitable protective groups are described in Greene et al. "Protective Groups in Organic Synthesis", 2nd ed., 1991, John Wiley and Sons, New York, N.Y., U.S.A. The compounds of this invention can be synthesized, generally following the synthetic schemes illustrated earlier in this application, as shown in the following examples or by modifying the exemplified syntheses by means known to those of ordinary skill in the art. Preparative examples refer to the preparation of intermediates useful in the synthesis of compounds of this invention; synthesis examples refer to the synthesis of compounds of this invention. Compound numbers refer to the table immediately following these examples.

Preparative Example 1

Preparation of 4-[2-(dimethylamino)ethoxy]phenyl isothiocyanate, an Intermediate for Compound 36A Diisopropylethylamine (344 mg, 2.66 mmol, 2.4 eq.) was added with stirring to a solution of 4-[2-(dimethylamino)ethoxy]aniline (200 mg, 1.11 mmol, 1 eq.) in tetrahydrofuran (2 mL) at 0° C., and then thiophosgene (153 mg, 1.33 mmol, 1.2 eq.) was added dropwise with stirring. The reaction mixture was allowed to warm to room temperature with stirring, and stirred at room temperature for 40 minutes, during which a precipitate formed. The tetrahydrofuran was removed under vacuum, and the residue was dissolved in ethyl acetate and washed with brine (3×10 mL), then the ethyl acetate layer dried over magnesium sulfate and the ethyl acetate evaporated to give 4-[2-(dimethylamino)ethoxy]phenyl isothiocyanate (0.20 g) as a dark brown oil, which was used without further purification.

Preparative Example 2

Preparation of 2-bromo-4'-[2-(dimethylamino)ethoxy]-acetophenone, an Intermediate for Compound 39A 2-(Dimethylamino)ethyl chloride hydrochloride (3.49 g, 23.2 mmol, 1.1 eq.) was added to a solution of 4'-hydroxyacetophenone (3.00 g, 22.0 mmol, 1 eq.) in acetone (100 mL), followed by the addition of potassium carbonate (9.12 g, 66.0 mmol, 3 eq.). The reaction mixture was heated under reflux overnight, cooled, and filtered; and the filtrate was concentrated and water (50 mL) was added, forming a cloudy solution. Hydrochloric acid (0.1N, 20 mL) was added, and the resulting clear solution was extracted three times with ethyl acetate. The aqueous phase was made basic with aqueous sodium hydroxide, forming a cloudy mixture, which was extracted with ethyl acetate (5×50 mL), then the ethyl acetate layer dried over magnesium sulfate and the ethyl acetate evaporated to give 4'-[2-(dimethylamino)ethoxy]acetophenone (2.90 g) as a light yellow oil, with identity and purity verified by LC-MS. Bromine (1.62 g, 10.1 mmol, 1.4 eq.) was added dropwise to a solution of the 4'-[2-(dimethylamino)ethoxy]acetophenone (1.5 g, 7.24 mmol) in acetic acid (5 mL) and the reaction mixture stirred at 24° C. for 3 hours, giving a dark red solution. The reaction mixture was cooled, water (5 mL) was added, and the mixture was lyophilized overnight. The crude 2-bromo-4'-[2-(dimethylamino)ethoxy]acetophenone was purified by preparative HPLC, followed by lyophilization of the appropriate fractions, to give 2-bromo-4'-[2-(dimethylamino)ethoxy]acetophenone (0.7 g) as an off-white solid.

Synthesis Example 1

Synthesis of 4-amino-5-(2,4-dimethoxybenzoyl)-2-[(4-ethoxyphenyl)amino]thiophene-3-carbonitrile, Compound 6A To a stirred solution of malononitrile (0.40 g, 6.1 mmol) in dimethylformamide (DMF) (5 mL) was added potassium carbonate (1.68 g, 12.2 mmol, 2 eq.). The mixture was stirred at room temperature for 15 minutes, and 4-ethoxyphenyl isothiocyanate (1.07 g, 6.1 mmol) was added. After stirring for an additional 30 minutes, 2-bromo-2',4'-dimethoxy-acetophenone (1.57 g, 6.1 mmol, 1 eq.) was added, and the mixture stirred at room temperature overnight. The solvent was removed under reduced pressure, and water (20 mL) was added to the residue. The resulting solid was collected by filtration and dried under vacuum to give 2.80 g of crude product as a yellow solid. This crude product was combined with two similar batches (altogether totaling 7.7 g of crude product) and purified by silica gel column chromatography, eluting with hexane/ethyl acetate (2:1 then 1:1) to give 4-amino-5-(2,4-dimethoxybenzoyl)-2-[(4-ethoxyphenyl)amino]thiophene-3-carbonitrile (2.2 g) as a yellow-brown solid. $^1$H NMR (DMSO-$d_6$): δ 10.24 (1H, s), 7.79 (2H, br.s), 7.21 (2H, d, J=8.6 Hz), 7.09 (1H, d, J=8.6 Hz), 6.91 (2H, d, J=9.0 Hz), 6.56 (1H, d, J=2.0 Hz), 6.49 (1H, dd, J=8.4 Hz, J=2.2 Hz), 4.02-3.96 (2H, q, J=7.0 Hz), 3.76 (3H, s), 1.92-1.57 (3H, t, J=7.0 Hz).

Synthesis Example 2

Synthesis of 4-amino-5-(4-chlorobenzoyl)-2-[(4-methoxyphenyl)amino]thiophene-3-carboxamide, Compound 1A To a stirred solution of 2-cyanoacetamide (3.0 g, 36 mmol) in DMF (50 mL) was added sodium hydride (60% in mineral oil, 1.43 g, 35.7 mmol, 1 eq.), and the mixture stirred at 0° C. for 1 hour, giving a clear solution. 4-Methoxyphenyl isothiocyanate (15.90 g, 35.7 mmol, 1 eq.) in DMF (10 mL) was added, and stirred for 30 minutes, then 2-bromo-4'-chloroacetophenone (8.33 g, 35.7 mmol, 1 eq.) and potassium carbonate (4.93 g, 35.7 mmol, 1 eq.) were added, and the mixture was stirred at room temperature for 1 week. Water (200 mL) was added; and the dark precipitate that formed was filtered, washed with water (3×50 mL), ethyl acetate (3×15 mL), and acetone (3×15 mL), then dried under vacuum to give 4-amino-5-(4-chlorobenzoyl)-2-[(4-methoxyphenyl)amino]thiophene-3-carboxamide (5.6 g) as a light orange solid. $^1$H NMR (DMSO-$d_6$): δ 9.97 (1H, s), 8.03 (2H, s), 7.54 (2H, d, J=8.2 Hz), 7.48 (2H, d, J=8.2 Hz), 7.41 (2H, s), 7.25 (2H, d, J=8.6 Hz), 6.94 (2H, d, J=8.6 Hz), 3.74 (3H, s).

The compounds of formula A as shown in the table below were prepared by one or more of the above methods, or similar methods not described in detail here. All of the compounds of formula A were analyzed to confirm identity and purity, using HPLC for purity, and one or more of mass spectrometry (using either positive or negative ionization) and NMR ($^1$H and/or $^{13}$C) for identity, and were confirmed to be the expected product in good purity. A number of other compounds of formula A were similarly prepared, and further compounds of formula A may be similarly prepared.

Representative compounds of formula A include ("exact mass" is of the parent compound; mass spectra were with positive ionization, blank indicates measurement not made):

| Compound | Structure | Exact mass, M | MS (m/z) |
|---|---|---|---|
| 1A | 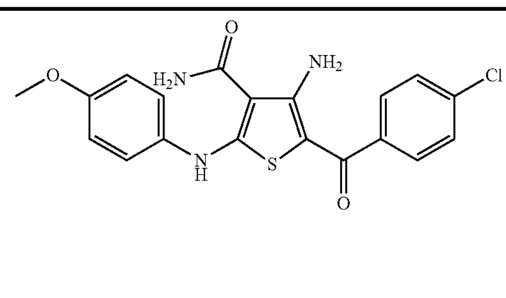 | 401 | 402 (M + H) |

-continued

| Compound | Structure | Exact mass, M | MS (m/z) |
|---|---|---|---|
| 2A | 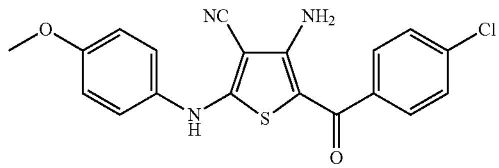 [SMILES: COc1ccc(Nc2sc(C(=O)c3ccc(Cl)cc3)c(N)c2C#N)cc1] | 383 | 384 (M + H) |
| 3A | 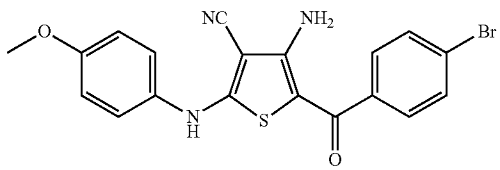 [SMILES: COc1ccc(Nc2sc(C(=O)c3ccc(Br)cc3)c(N)c2C#N)cc1] | 427 | 428 (M + H) |
| 4A | 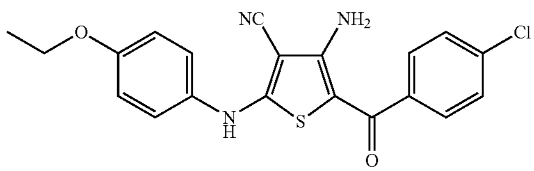 [SMILES: CCOc1ccc(Nc2sc(C(=O)c3ccc(Cl)cc3)c(N)c2C#N)cc1] | 397 | 398 (M + H) |
| 5A | 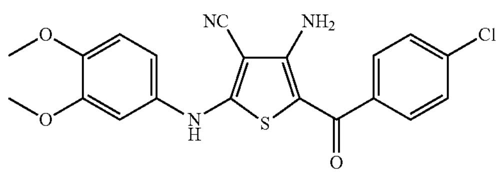 [SMILES: COc1ccc(Nc2sc(C(=O)c3ccc(Cl)cc3)c(N)c2C#N)cc1OC] | 413 | 414 (M + H) |
| 6A | 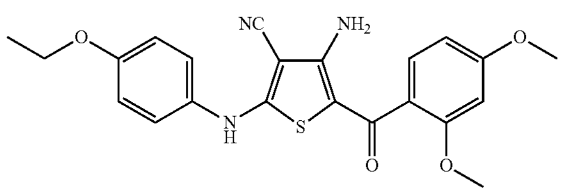 [SMILES: CCOc1ccc(Nc2sc(C(=O)c3ccc(OC)cc3OC)c(N)c2C#N)cc1] | 423 | 424 (M + H) |
| 7A | 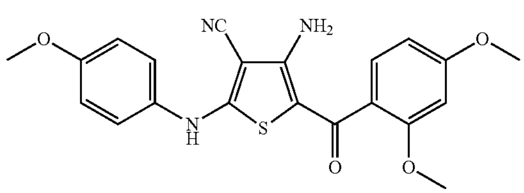 | 409 | 410 (M + H) |
| 8A | 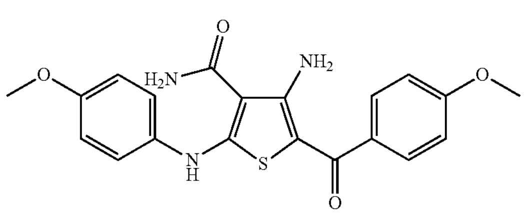 | 397 | 398 (M + H) |
| 9A | 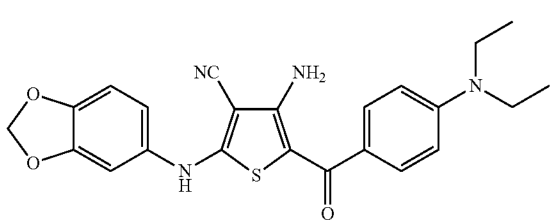 [SMILES: CCN(CC)c1ccc(C(=O)c2sc(Nc3ccc4c(c3)OCO4)c(C#N)c2N)cc1] | 434 | 435 (M + H) |

-continued
| Compound | Structure | Exact mass, M | MS (m/z) |
|---|---|---|---|
| 10A | 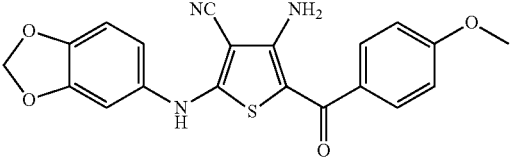 [SMILES: COc1ccc(C(=O)c2sc(Nc3ccc4c(c3)OCO4)c(C#N)c2N)cc1] | 393 | 394 (M + H) |
| 11A | 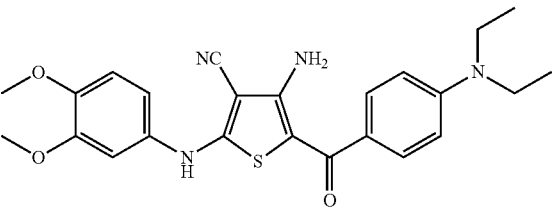 [SMILES: CCN(CC)c1ccc(C(=O)c2sc(Nc3ccc(OC)c(OC)c3)c(C#N)c2N)cc1] | 450 | 451 (M + H) |
| 12A | 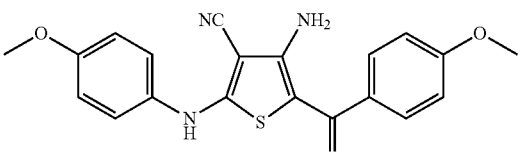 | 379 | 380 (M + H) |
| 13A | 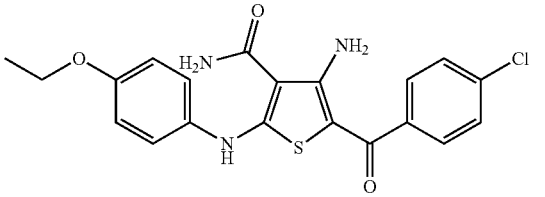 [SMILES: CCOc1ccc(Nc2sc(C(=O)c3ccc(Cl)cc3)c(N)c2C(N)=O)cc1] | 415 | 416 (M + H) |
| 14A | 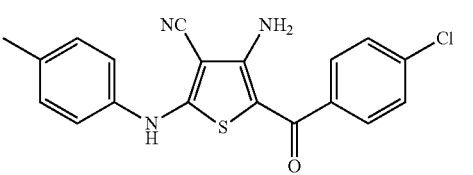 [SMILES: Cc1ccc(Nc2sc(C(=O)c3ccc(Cl)cc3)c(N)c2C#N)cc1] | 367 | 368 (M − H) |
| 15A | 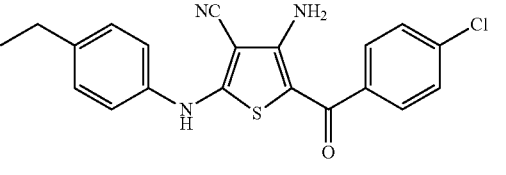 [SMILES: CCc1ccc(Nc2sc(C(=O)c3ccc(Cl)cc3)c(N)c2C#N)cc1] | 381 | 382 (M − H) |
| 16A | 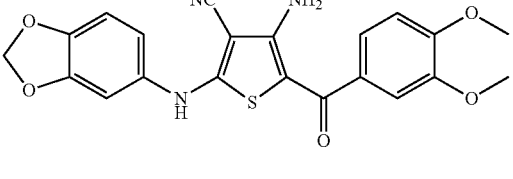 | 423 | 424 (M + H) |
| 17A | 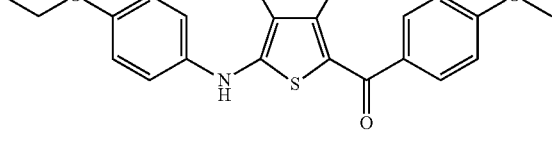 | 393 | 394 (M + H) |

-continued

| Compound | Structure | Exact mass, M | MS (m/z) |
|---|---|---|---|
| 19A | 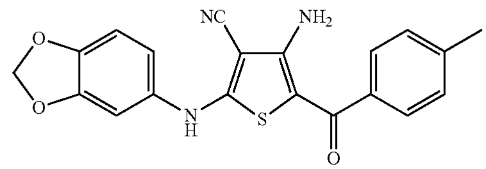 [SMILES: Cc1ccc(C(=O)c2sc(Nc3ccc4c(c3)OCO4)c(C#N)c2N)cc1] | 377 | 378 (M + H) |
| 20A | 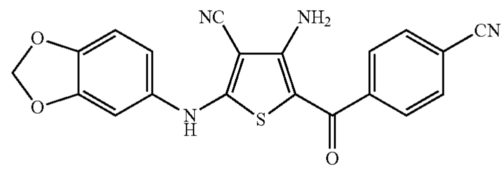 [SMILES: N#Cc1ccc(C(=O)c2sc(Nc3ccc4c(c3)OCO4)c(C#N)c2N)cc1] | 388 | 389 (M + H) |
| 21A | 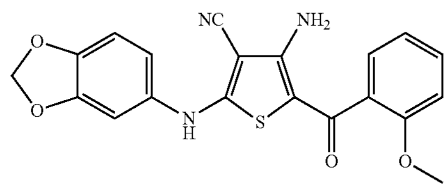 [SMILES: COc1ccccc1C(=O)c1sc(Nc2ccc3c(c2)OCO3)c(C#N)c1N] | 393 | 394 (M + H) |
| 22A | 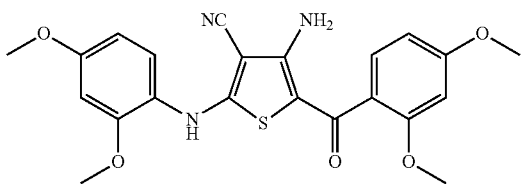 | 439 | 440 (M + H) |
| 23A | 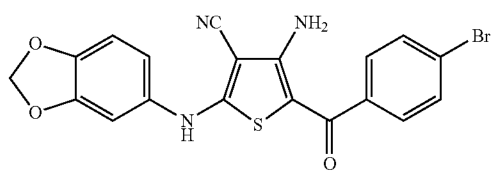 [SMILES: N#Cc1c(Nc2ccc3c(c2)OCO3)sc(C(=O)c2ccc(Br)cc2)c1N] | 441 | 442 (M + H) |
| 24A | 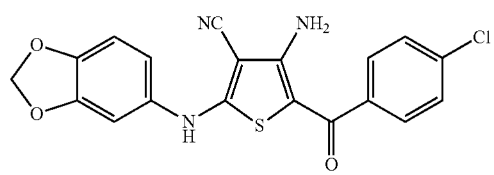 [SMILES: N#Cc1c(Nc2ccc3c(c2)OCO3)sc(C(=O)c2ccc(Cl)cc2)c1N] | 397 | 398 (M + H) |
| 25A | 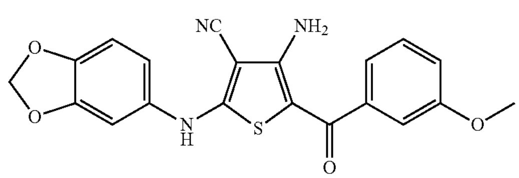 [SMILES: COc1cccc(C(=O)c2sc(Nc3ccc4c(c3)OCO4)c(C#N)c2N)c1] | 393 | 394 (M + H) |
| 26A | 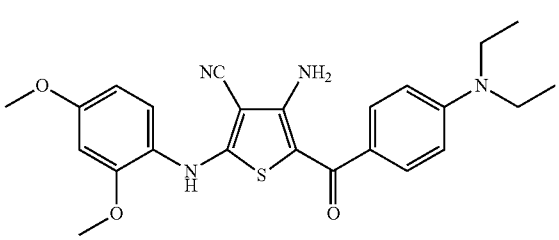 [SMILES: CCN(CC)c1ccc(C(=O)c2sc(Nc3ccc(OC)cc3OC)c(C#N)c2N)cc1] | 450 | 451 (M + H) |

US 8,410,163 B2
-continued
| Compound | Structure | Exact mass, M | MS (m/z) |
|---|---|---|---|
| 27A | 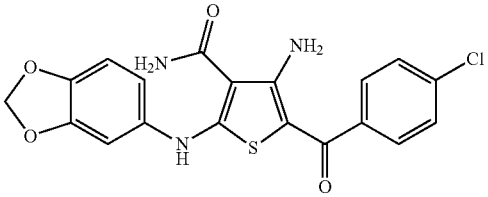 [SMILES: NC(=O)c1c(Nc2ccc3c(c2)OCO3)sc(C(=O)c2ccc(Cl)cc2)c1N] | 415 | |
| 28A | 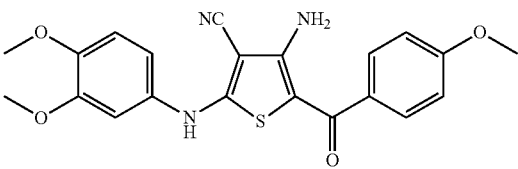 | 409 | 410 (M − H) |
| 29A | 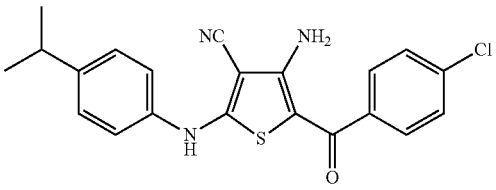 [SMILES: CC(C)c1ccc(Nc2sc(C(=O)c3ccc(Cl)cc3)c(N)c2C#N)cc1] | 395 | 396 (M − H) |
| 30A | 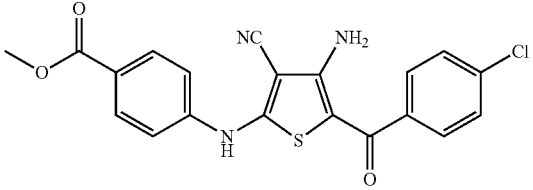 [SMILES: COC(=O)c1ccc(Nc2sc(C(=O)c3ccc(Cl)cc3)c(N)c2C#N)cc1] | 411 | 412 (M + H) |
| 31A | 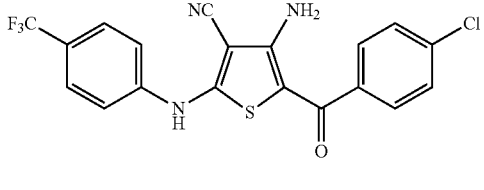 [SMILES: N#Cc1c(Nc2ccc(C(F)(F)F)cc2)sc(C(=O)c2ccc(Cl)cc2)c1N] | 421 | 422 (M + H) |
| 32A | 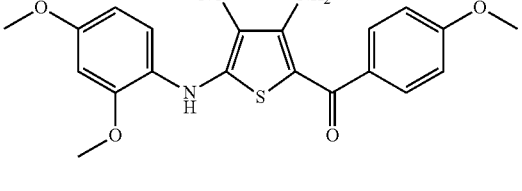 | 409 | 410 (M + H) |
| 33A | 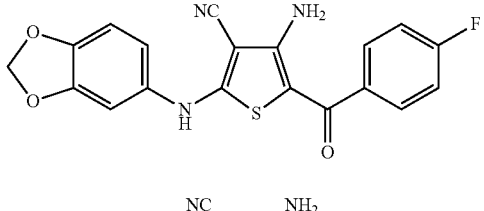 | 381 | 382 (M + H) |
| 34A | 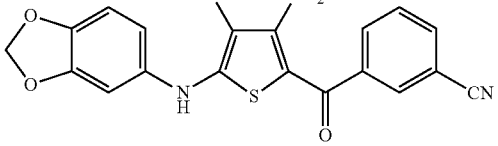 | 388 | 389 (M + H) |

-continued

| Compound | Structure | Exact mass, M | MS (m/z) |
|---|---|---|---|
| 35A | 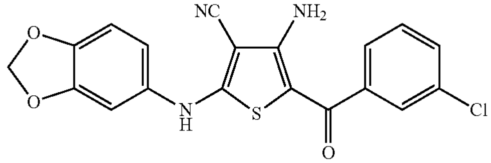 [SMILES: N#Cc1c(Nc2ccc3c(c2)OCO3)sc(C(=O)c2cccc(Cl)c2)c1N] | 397 | 398 (M + H) |
| 36A | 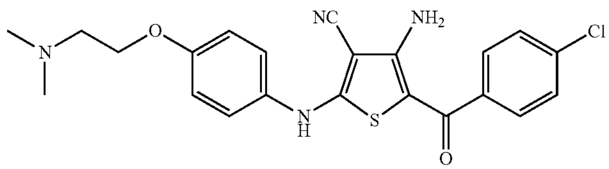 [SMILES: CN(C)CCOc1ccc(Nc2sc(C(=O)c3ccc(Cl)cc3)c(N)c2C#N)cc1] | 440 | 441 (M + H) |
| 37A | 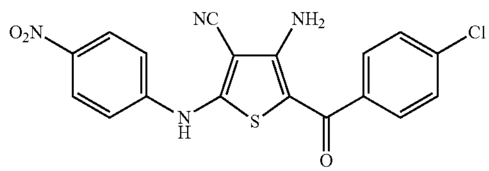 [SMILES: N#Cc1c(Nc2ccc([N+](=O)[O-])cc2)sc(C(=O)c2ccc(Cl)cc2)c1N] | 398 | 399 (M + H) |
| 38A | 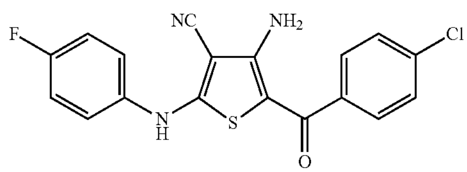 [SMILES: N#Cc1c(Nc2ccc(F)cc2)sc(C(=O)c2ccc(Cl)cc2)c1N] | 371 | 372 (M + H) |
| 39A | 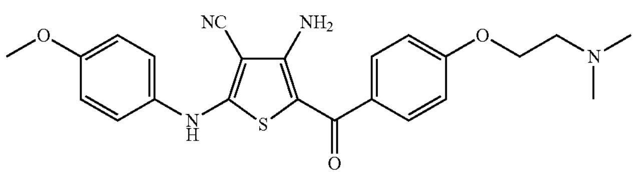 | 436 | 437 (M + H) |
| 40A | 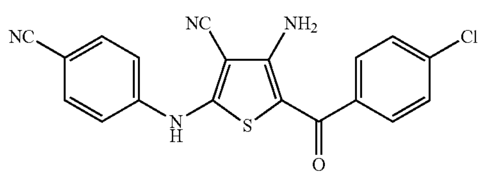 [SMILES: N#Cc1ccc(Nc2sc(C(=O)c3ccc(Cl)cc3)c(N)c2C#N)cc1] | 378 | 379 (M + H) |
| 41A | 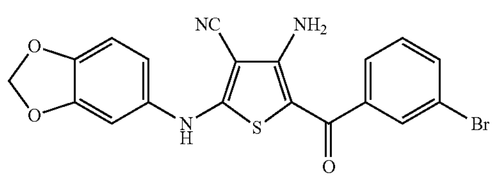 [SMILES: N#Cc1c(Nc2ccc3c(c2)OCO3)sc(C(=O)c2cccc(Br)c2)c1N] | 441 | 442 (M + H) |

Other compounds of the invention may be similarly prepared, or may be prepared using methods well known to a person of ordinary skill in the art having regard to that skill and this disclosure.

In vitro Examples

The following examples illustrate the cytotoxic/cytostatic effect of the compounds against human cancer cell lines in vitro. These results are considered predictive of efficacy in human cancer chemotherapy, as other anticancer agents tested in these assays have shown anticancer activity in humans.

The cell lines A549 (human lung adenocarcinoma), OVCAR-3 (human ovarian carcinoma), HL60 (human promyelocytic leukemia), DLD1 (human colon adenocarcinoma) and HCT116 (human colon carcinoma) were obtained from the American Type Culture Collection, Manassas, Va., U.S.A. All products were used in accordance with manufacturer's directions. The histone phosphorylation (p-H3) assay was conducted in duplicate and the cytotoxicity assays were conducted in triplicate, in each case with solvent control.

In vitro Example 1

Cytotoxicity Assays

Log-phase cells were trypsinized, collected by centrifugation, and resuspended in a small volume of fresh medium, and the density of viable cells was determined following Trypan Blue staining. Cells were diluted in fresh media, the test compounds (concentrations between 0.1 µM and 200 µM, dissolved in DMSO, 50 µL) added immediately after dilution to achieve a final DMSO concentration of 0.5%, then the suspensions added at 150 µL/well to 96-well plates, and incubated overnight to allow attachment in the case of adherent cells. The cells were cultured for three days (about three doubling times). The cells were then collected by centrifugation, and 100 µL of the culture supernatant was replaced by the CellTiter-Glo reagent. After incubation for 15 minutes at room temperature, the plate was read with a luminometer. Compounds of formula A showed the following cytotoxicity in these assays. The table gives cytotoxicity $IC_{50}$s in µM, rounded to 1 significant figure.

| Compound | A549 | OVCAR-3 | HL-60 | DLD1 | HCT116 |
|---|---|---|---|---|---|
| 1A | 0.01 | 0.01 | 0.01 | 0.007 | 0.01 |
| 2A | 0.01 | 0.02 | 0.01 | 0.006 | 0.01 |
| 3A | 0.02 | | | | |
| 4A | 0.02 | 0.03 | 0.04 | 0.03 | 0.09 |
| 5A | 0.02 | 0.02 | 0.02 | 0.02 | 0.02 |
| 6A | 0.03 | | 0.05 | | 0.03 |
| 7A | 0.03 | | 0.02 | | 0.01 |
| 8A | 0.04 | 0.01 | 0.03 | 0.007 | |
| 9A | 0.04 | 0.02 | 0.04 | 0.02 | 0.04 |
| 10A | 0.04 | 0.04 | 0.04 | 0.03 | |
| 11A | 0.05 | | | | |
| 12A | 0.05 | 0.03 | 0.04 | 0.04 | 0.04 |
| 13A | 0.06 | | 0.03 | | |
| 14A | 0.1 | | 0.07 | | 0.08 |
| 15A | 0.1 | | 0.09 | | |
| 16A | 0.1 | | 0.06 | | |
| 17A | 0.1 | | 0.1 | | |
| 19A | 0.2 | | | | |
| 20A | 0.2 | | | | |
| 21A | 0.2 | | | | |
| 22A | 0.2 | | | | |
| 23A | 0.3 | | | | |
| 24A | 0.3 | | 0.08 | | |
| 25A | 0.5 | | | | |
| 26A | 0.5 | | | | |
| 27A | 0.6 | 0.3 | 0.2 | | 0.6 |
| 28A | 0.7 | | | | |
| 29A | 0.8 | | | | |
| 30A | 1 | | | | |
| 31A | 1 | | | | |
| 32A | 1 | | | | |
| 33A | 1 | | | | |
| 34A | 1 | | | | |
| 35A | 1 | | | | |
| 36A | 1 | | | | |
| 37A | 2 | | | | |
| 38A | 2 | | | | |
| 39A | 2 | | | | |
| 40A | 2 | | | | |
| 41A | 2 | | | | |

In vitro Example 2

Cell Cycle Analysis in A549 Cells

Log-phase cells were seeded in a 75-mL flask overnight to allow cell attachment, with the seeding density chosen so that the cell culture would be less than 80% confluent on the day of harvest. The test compounds were added (dissolved in DMSO) at about $IC_{80}$ to achieve a final DMSO concentration of 0.1%, and the cells then incubated further for one, two, or three days. Following incubation, the cells were harvested, washed with cold PBS, fixed in 75% aqueous ethanol, and stored at −20° C. until further analysis. To determine the cellular DNA content, which reflects the cell cycle status, the fixed cells were washed twice with phosphate-buffered saline and then treated with RNase for 30 minutes at 37° C. They were then stained with propidium iodide, followed by FACS analysis on a Becton Dickinson FACSCalibur system. Of the 41 compounds of formula A described above, 35 were tested and 30 showed G2/M cell cycle arrest.

In vitro Example 3

Histone Phosphorylation (p-H3) Assay

Log phase A549 cells were seeded in a 96-well plate and allowed to attach overnight. The test compounds were diluted in DMSO (8 concentrations with serial 3-fold dilutions) and added to the cells (0.5% DMSO final concentration), and the cells incubated for 4 hr. The cells were then washed three times with cold phosphate-buffered saline (PBS), and lysis buffer was added. After 30 min shaking at 4° C. and centrifugation, the supernatants were transferred to a nitrocellulose membrane by a "dot-blot" apparatus. After washing the wells, the membrane was processed for Western blot. Detection of p-H3 and β-actin was performed on the same membrane with primary rabbit anti-p-H3 and mouse anti-β-actin antibodies followed by secondary goat anti-rabbit IRDye800 and goat anti-mouse AlexaFluor 680 antibodies. The membranes were scanned on an Odyssey scanner. Eleven of the compounds 1A to 15A were tested, with $IC_{50}$s ranging from 0.02 µM (compound 2A) to 0.5 µM (compound 15A), the trend of inhibitory potency being generally the same as that of cytotoxicity.

In vitro Example 4

Inhibition of Tubulin Polymerization

Compounds 2A, 9A, 12A, 14A, and 21A were tested for inhibition of tubulin polymerization in a cell-free fluorescence assay, with all compounds showing inhibition of tubulin polymerization. Compounds 2A, 4A to 10A, 12A, 14A, 15A, 19A, 29A, 30A, and 40A were tested for inhibition of tubulin polymerization in A549 cells by immunomicroscopy and cell fractionation, with $IC_{50}$s ranging from 0.009 µM (compound 7A) to 2 µM (compound 30A), the trend of inhibitory potency being generally the same as that of cytotoxicity. Compound 40A was inactive in this assay.

In vitro Example 5

Other Assays

Compounds 2A, 9A, and 12A were tested for cross-resistance in the P388 (mouse leukemia) cell line, by assaying its cytotoxicity in both P388 and P388/ADR (doxorubicin-resistant) cells. Where doxorubicin itself showed a 260-fold resistance ratio, vinblastine showed a 50-fold resistance ratio, and colchicine (a tubulin inhibitor) showed a 70-fold resistance ratio, compounds 2A, 9A, and 12A all showed less than 2-fold resistance ratios. Several of the more cytotoxic compounds of formula A were tested and found not to be substrates for P-glycoprotein, an efflux pump commonly associated with multidrug-resistance in cancer cells.

In vivo Examples

In vivo Example 1

HL60 Xenograft Assay, Oral Administration

Male athymic nu/nu mice, 6-8 weeks old (about 20 g), were implanted subcutaneously in the right fore flank with about $1 \times 10^7$ cells of the HL60 (human promyelocytic leukemia) line that had been grown in antibiotic-free medium for at least two passages. About 6 days after tumor implantation, when the tumor weight was about 50-250 mg, the mice were assigned to treatment groups. Test compounds were suspended at 20 mg/mL in 0.55 wt. % aqueous carboxymethylcellulose. Groups of mice were treated with compounds 2A, 9A, and 12A at 200 mg/Kg by gavage once/day on days 1-5 and 8-10 from the start of treatment, with vehicle control. Tumor growth inhibition was measured on the last day of treatment. All three compounds tested were active in this assay, with compound 2A causing 46% inhibition of tumor growth compared to vehicle, compound 9A causing 43% inhibition, and compound 12A causing 66% inhibition.

In vivo Example 2

HCT116 Xenograft Assay, Oral Administration

Male athymic nu/nu mice, 6-8 weeks old (about 20 g), were implanted subcutaneously in the right fore flank with about $1 \times 10^7$ cells of the HCT116 (human colon carcinoma) line that had been grown in antibiotic-free medium for at least two passages. About 14-21 days after tumor transplantation, when the tumor weight was about 50-250 mg, the mice were assigned to treatment groups. Test compounds were suspended at 20 mg/mL in 0.55 wt. % aqueous carboxymethylcellulose. Groups of mice were treated with compounds 2A, 9A, and 12A at 200 mg/Kg by gavage once/day on days 1-5 and 8-12 from the start of treatment, with vehicle control. Tumor growth inhibition was measured 2 days after the last day of treatment. All three compounds tested were active in this assay, with compound 2A causing 35% inhibition of tumor growth compared to vehicle, compound 9A causing 36% inhibition, and compound 12A causing 46% inhibition.

In vivo Example 3

HL60 Xenograft Assay, Oral Administration

The experiment was conducted generally as described in In vivo Example 1. Groups of mice were treated with compounds 5A, 6A, 7A, 8A, and 10A at 200 mg/Kg by gavage once/day on days 1-5 and 8-10 from the start of treatment, with vehicle control. Tumor growth inhibition was measured the day after the last day of treatment. Four of the five compounds tested were active in this assay, with compound 5A causing 45% inhibition of tumor growth compared to vehicle, compound 6A causing 89% inhibition, compound 7A causing 45% inhibition, and compound 10A causing 67% inhibition; while compound 8A caused 10% inhibition (not statistically significant).

Formulation Examples

Formulation Example 1

Formulation for Oral Administration

A solid formulation for oral administration is prepared by combining the following:

| | |
|---|---|
| Compound of this invention | 25.0% w/w |
| Magnesium stearate | 0.5% w/w |
| Starch | 2.0% w/w |
| Hydroxypropylmethylcellulose | 1.0% w/w |
| Microcrystalline cellulose | 71.5% w/w | and the mixture is compressed to form tablets or filled into hard gelatin capsules containing, for example, 100 mg of the compound of this invention. Tablets may be coated, if desired, by applying a suspension of a film-forming agent (for example, hydroxypropylmethylcellulose), pigment (for example, titanium dioxide), and plasticizer (for example, diethyl phthalate), and drying the film by evaporation of the solvent.

Formulation Example 2

Formulation for IV Administration

A formulation for IV administration is prepared by dissolving a compound of this invention, for example as a pharmaceutically acceptable salt, to a concentration of 1% w/v in phosphate-buffered saline; and the solution is sterilized, for example by sterile filtration, and sealed in sterile containers containing, for example, 100 mg of a compound of this invention.

Alternatively, a lyophilized formulation is prepared by dissolving a compound of this invention, again for example as a pharmaceutically acceptable salt, in a suitable buffer, for example the phosphate buffer of the phosphate-buffered saline mentioned above, optionally with the addition of a bulking agent and other pharmaceutically useful excipients, sterilizing the solution and dispensing it into suitable sterile vials, lyophilizing the solution to remove the water, and sealing the vials. The lyophilized formulation is reconstituted by the addition of sterile water, and the reconstituted solution may be further diluted for administration with a solution such as 0.9% sodium chloride intravenous infusion or 5% dextrose intravenous infusion.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

The invention claimed is:

1. A method for inhibiting tubulin polymerization comprising administering to a patient in need thereof a therapeutically effective amount of a compound of formula A

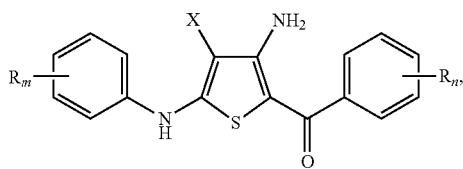

or its salt,
where:
X is CN or CONH₂;
m and n independently are 0, 1, 2, or 3, provided that at least one of m and n is not 0; and
each R independently is selected from the group consisting of halo, cyano, nitro, optionally substituted alkyl, —OR', —SR', —C(O)OR', and —NR'R", where R' is optionally substituted alkyl, and R" is hydrogen or alkyl, or two adjacent R groups on the same phenyl group together are methylenedioxy.

2. The method of claim 1, wherein the compound is selected from:
4-amino-5-(4-chlorobenzoyl)-2-[(4-methoxyphenyl)amino]thiophene-3-carboxamide,
4-amino-5-(4-chlorobenzoyl)-2-[(4-ethoxyphenyl)amino]thiophene-3-carbonitrile,
4-amino-5-(4-methoxybenzoyl)-2-[(4-methoxyphenyl)amino]thiophene-3-carbonitrile,
4-amino-5-(4-chlorobenzoyl)-2-[(4-ethoxyphenyl)amino]thiophene-3-carbonitrile, and
4-amino-5-(4-chlorobenzoyl)-2-[(4-fluorophenyl)amino]thiophene-3-carbonitrile,
and their salts.

3. A compound selected from:
4-amino-5-(4-chlorobenzoyl)-2-[(4-methoxyphenyl)amino]thiophene-3-carbonitrile,
4-amino-5-(4-bromobenzoyl)-2-[(4-methoxyphenyl)amino]thiophene-3-carbonitrile,
4-amino-5-(4-chlorobenzoyl)-2-[(3,4-dimethoxyphenyl)amino]thiophene-3-carbonitrile,
4-amino-5-(2,4-dimethoxybenzoyl)-2-[(4-ethoxyphenyl)amino]thiophene-3-carbonitrile,
4-amino-5-(4-methoxybenzoyl)-2-[(4-methoxyphenyl)amino]thiophene-3-carboxamide,
4-amino-5-[4-(dimethylamino)benzoyl]-2-[(3,4-methylenedioxyphenyl)amino]thiophene-3-carbonitrile,
4-amino-5-(4-methoxybenzoyl)-2-[(3,4-methylenedioxyphenyl)amino]thiophene-3-carbonitrile,
4-amino-5-[4-(dimethylamino)benzoyl]-2-[(3,4-dimethoxyphenyl)amino]thiophene-3-carbonitrile,
4-amino-5-(4-chlorobenzoyl)-2-[(4-ethoxyphenyl)amino]thiophene-3-carboxamide,
4-amino-5-(4-chlorobenzoyl)-2-[(4-methylphenyl)amino]thiophene-3-carbonitrile,
4-amino-5-(3,4-dimethoxybenzoyl)-2-[(3,4-methylenedioxyphenyl)amino]thiophene-3-carbonitrile,
4-amino-5-(4-methylbenzoyl)-2-[(3,4-methylenedioxyphenyl)amino]thiophene-3-carbonitrile,
4-amino-5-(4-cyanobenzoyl)-2-[(3,4-methylenedioxyphenyl)amino]thiophene-3-carbonitrile,
4-amino-5-(2-methoxybenzoyl)-2-[(3,4-methylenedioxyphenyl)amino]thiophene-3-carbonitrile,
4-amino-5-(2,4-dimethoxybenzoyl)-2-[(2,4-dimethoxyphenyl)amino]thiophene-3-carbonitrile,
4-amino-5-(4-bromobenzoyl)-2-[(3,4-methylenedioxyphenyl)amino]thiophene-3-carbonitrile,
4-amino-5-(4-chlorobenzoyl)-2-[(3,4-methylenedioxyphenyl)amino]thiophene-3-carbonitrile,
4-amino-5-(3-methoxybenzoyl)-2-[(3,4-methylenedioxyphenyl)amino]thiophene-3-carbonitrile,
4-amino-5-[4-(dimethylamino)benzoyl]-2-[(2,4-dimethoxyphenyl)amino]thiophene-3-carbonitrile,
4-amino-5-(4-methoxybenzoyl)-2-[(3,4-dimethoxyphenyl)amino]thiophene-3-carbonitrile,
4-amino-5-(4-chlorobenzoyl)-2-[(4-isopropylphenyl)amino]thiophene-3-carbonitrile,
4-amino-5-(4-chlorobenzoyl)-2-{[4-(methoxycarbonyl)phenyl]amino}thiophene-3-carbonitrile,
4-amino-5-(4-chlorobenzoyl)-2-{[4-(trifluoromethyl)phenyl]amino}thiophene-3-carbonitrile,
4-amino-5-(4-methoxybenzoyl)-2-[(2,4-dimethoxyphenyl)amino]thiophene-3-carbonitrile,
4-amino-5-(4-fluorobenzoyl)-2-[(3,4-methylenedioxyphenyl)amino]thiophene-3-carbonitrile,
4-amino-5-(3-cyanobenzoyl)-2-[(3,4-methylenedioxyphenyl)amino]thiophene-3-carbonitrile,
4-amino-5-(3-chlorobenzoyl)-2-[(3,4-methylenedioxyphenyl)amino]thiophene-3-carbonitrile,
4-amino-5-(4-chlorobenzoyl)-2-({4-[2-(dimethylamino)ethoxy]phenyl}amino)thiophene-3-carbonitrile,
4-amino-5-(4-chlorobenzoyl)-2-[(4-nitrophenyl)amino]thiophene-3-carbonitrile,
4-amino-5-{4-[2-(dimethylamino)ethoxy]benzoyl}-2-[(4-methoxyphenyl)amino]thiophene-3-carbonitrile,
4-amino-5-(4-chlorobenzoyl)-2-[(4-cyanophenyl)amino]thiophene-3-carbonitrile, and
4-amino-5-(3-bromobenzoyl)-2-[(3,4-methylenedioxyphenyl)amino]thiophene-3-carbonitrile,
and their salts.

4. The compound of claim 3 that is selected from:
4-amino-5-(4-chlorobenzoyl)-2-[(4-methoxyphenyl)amino]thiophene-3-carbonitrile,
4-amino-5-(4-bromobenzoyl)-2-[(4-methoxyphenyl)amino]thiophene-3-carbonitrile,
4-amino-5-(4-chlorobenzoyl)-2-[(3,4-dimethoxyphenyl)amino]thiophene-3-carbonitrile,
4-amino-5-(2,4-dimethoxybenzoyl)-2-[(4-ethoxyphenyl)amino]thiophene-3-carbonitrile,
4-amino-5-(4-methoxybenzoyl)-2-[(4-methoxyphenyl)amino]thiophene-3-carboxamide,
4-amino-5-[4-(dimethylamino)benzoyl]-2-[(3,4-methylenedioxyphenyl)amino]thiophene-3-carbonitrile,
4-amino-5-(4-methoxybenzoyl)-2-[(3,4-methylenedioxyphenyl)amino]thiophene-3-carbonitrile,
4-amino-5-[4-(dimethylamino)benzoyl]-2-[(3,4-dimethoxyphenyl)amino]thiophene-3-carbonitrile,
4-amino-5-(4-chlorobenzoyl)-2-[(4-ethoxyphenyl)amino]thiophene-3-carboxamide,
4-amino-5-(4-chlorobenzoyl)-2-[(4-methylphenyl)amino]thiophene-3-carbonitrile, and
4-amino-5-(3,4-dimethoxybenzoyl)-2-[(3,4-methylenedioxyphenyl)amino]thiophene-3-carbonitrile,
and their salts.

5. The compound of claim 4 that is 4-amino-5-(2,4-dimethoxybenzoyl)-2-[(4-ethoxyphenyl)amino]thiophene-3-carbonitrile or its salt.

6. The compound of claim 4 that is 4-amino-5-(4-methoxybenzoyl)-2-[(3,4-methylenedioxyphenyl)amino]thiophene-3-carbonitrile or its salt.

7. A compound of claim 3 selected from:
4-amino-5-(4-bromobenzoyl)-2-[(4-methoxyphenyl)amino]thiophene-3-carbonitrile, 4-amino-5-(4-chlorobenzoyl)-2-[(3,4-dimethoxyphenyl)amino]thiophene-3-carbonitrile,
4-amino-5-(4-methoxybenzoyl)-2-[(4-methoxyphenyl)amino]thiophene-3-carboxamide,
4-amino-5-[4-(dimethylamino)benzoyl]-2-[(3,4-methylenedioxyphenyl)amino]thiophene-3-carbonitrile,
4-amino-5-(4-methoxybenzoyl)-2-[(3,4-methylenedioxyphenyl)amino]thiophene-3-carbonitrile,
4-amino-5-[4-(dimethylamino)benzoyl]-2-[(3,4-dimethoxyphenyl)amino]thiophene-3-carbonitrile,
4-amino-5-(4-chlorobenzoyl)-2-[(4-ethoxyphenyl)amino]thiophene-3-carboxamide,
4-amino-5-(4-chlorobenzoyl)-2-[(4-methylphenyl)amino]thiophene-3-carbonitrile,
4-amino-5-(3,4-dimethoxybenzoyl)-2-[(3,4-methylenedioxyphenyl)amino]thiophene-3-carbonitrile,
4-amino-5-(4-methylbenzoyl)-2-[(3,4-methylenedioxyphenyl)amino]thiophene-3-carbonitrile,
4-amino-5-(4-cyanobenzoyl)-2-[(3,4-methylenedioxyphenyl)amino]thiophene-3-carbonitrile,
4-amino-5-(2-methoxybenzoyl)-2-[(3,4-methylenedioxyphenyl)amino]thiophene-3-carbonitrile,
4-amino-5-(2,4-dimethoxybenzoyl)-2-[(2,4-dimethoxyphenyl)amino]thiophene-3-carbonitrile,
4-amino-5-(4-bromobenzoyl)-2-[(3,4-methylenedioxyphenyl)amino]thiophene-3-carbonitrile,
4-amino-5-(4-chlorobenzoyl)-2-[(3,4-methylenedioxyphenyl)amino]thiophene-3-carbonitrile,
4-amino-5-(3-methoxybenzoyl)-2-[(3,4-methylenedioxyphenyl)amino]thiophene-3-carbonitrile,
4-amino-5-[4-(dimethylamino)benzoyl]-2-[(2,4-dimethoxyphenyl)amino]thiophene-3-carbonitrile,
4-amino-5-(4-methoxybenzoyl)-2-[(3,4-dimethoxyphenyl)amino]thiophene-3-carbonitrile,
4-amino-5-(4-chlorobenzoyl)-2-[(4-isopropylphenyl)amino]thiophene-3-carbonitrile,
4-amino-5-(4-chlorobenzoyl)-2-{[4-(methoxycarbonyl)phenyl]amino}thiophene-3-carbonitrile,
4-amino-5-(4-chlorobenzoyl)-2-{[4-(trifluoromethyl)phenyl]amino}thiophene-3-carbonitrile,
4-amino-5-(4-methoxybenzoyl)-2-[(2,4-dimethoxyphenyl)amino]thiophene-3-carbonitrile,
4-amino-5-(4-fluorobenzoyl)-2-[(3,4-methylenedioxyphenyl)amino]thiophene-3-carbonitrile,
4-amino-5-(3-cyanobenzoyl)-2-[(3,4-methylenedioxyphenyl)amino]thiophene-3-carbonitrile,
4-amino-5-(3-chlorobenzoyl)-2-[(3,4-methylenedioxyphenyl)amino]thiophene-3-carbonitrile,
4-amino-5-(4-chlorobenzoyl)-2-({4-[2-(dimethylamino)ethoxy]phenyl}amino)thiophene-3-carbonitrile,
4-amino-5-(4-chlorobenzoyl)-2-[(4-nitrophenyl)amino]thiophene-3-carbonitrile,
4-amino-5-{4-[2-(dimethylamino)ethoxy]benzoyl}-2-[(4-methoxyphenyl)amino]thiophene-3-carbonitrile,
4-amino-5-(4-chlorobenzoyl)-2-[(4-cyanophenyl)amino]thiophene-3-carbonitrile, and
4-amino-5-(3-bromobenzoyl)-2-[(3,4-methylenedioxyphenyl)amino]thiophene-3-carbonitrile,
and their salts.

8. A method for inhibiting tubulin polymerization comprising administering to a patient in need thereof a therapeutically effective amount of a compound of claim 3.

9. A method for treating cancer comprising administering to a patient in need thereof a therapeutically effective amount of a compound of claim 3, wherein the cancer is selected from the group consisting of lung cancer, ovarian cancer, leukemia, and colon cancer.

10. A method for treating cancer comprising administering to a patient in need thereof a therapeutically effective amount of a compound of formula A

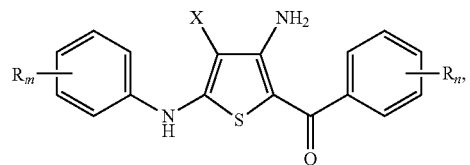

or its salt,
where:
X is CN or $CONH_2$;
m and n independently are 0, 1, 2, or 3, provided that at least one of m and n is not 0; and
each R independently is selected from the group consisting of halo, cyano, nitro, optionally substituted alkyl, —OR', —SR', —C(O)OR', and —NR'R", where R' is optionally substituted alkyl, and R" is hydrogen or alkyl, or two adjacent R groups on the same phenyl group together are methylenedioxy, wherein the cancer is selected from the group consisting of lung cancer, ovarian cancer, leukemia, and colon cancer.

11. The method of claim 10 wherein the compound is selected from:
4-amino-5-(4-chlorobenzoyl)-2-[(4-methoxyphenyl)amino]thiophene-3-carboxamide,
4-amino-5-(4-chlorobenzoyl)-2-[(4-ethoxyphenyl)amino]thiophene-3-carbonitrile,
4-amino-5-(4-methoxybenzoyl)-2-[(4-methoxyphenyl)amino]thiophene-3-carbonitrile,
4-amino-5-(4-chlorobenzoyl)-2-[(4-ethoxyphenyl)amino]thiophene-3-carbonitrile, and
4-amino-5-(4-chlorobenzoyl)-2-[(4-fluorophenyl)amino]thiophene-3-carbonitrile,
and their salts.

12. The method of any one of claims 1 and 8-10 further comprising administering to the patient another anticancer therapy.

13. A pharmaceutical composition comprising a compound of any one of claims 3 to 6 and 7.

* * * * *